US012233085B2

United States Patent
Liu et al.

(10) Patent No.: US 12,233,085 B2
(45) Date of Patent: Feb. 25, 2025

(54) APPLICATION OF HYALURONIC ACID IN PREPARING MEDICINES FOR PREVENTING OR TREATING FERROPTOSIS-RELATED DISEASES

(71) Applicants: ACADEMY OF MILITARY MEDICAL SCIENCES, ACADEMY OF MILITARY SCIENCES OF CHINESE PLA, Beijing (CN); BEIJING JIUYU ONCOLGY CO LTD, Beijing (CN)

(72) Inventors: Zhiqiang Liu, Beijing (CN); Zengqiang Yuan, Beijing (CN); Xiaowen Xing, Beijing (CN); Bingshui Xiu, Beijing (CN); Shihong Liu, Beijing (CN)

(73) Assignees: ACADEMY OF MILITARY MEDICAL SCIENCES, ACADEMY OF MILITARY SCIENCES OF CHINESE PLA, Beijing (CN); BEIJING JIUYU ONCOLGY CO LTD, Beijing (CN)

( * ) Notice: Subject to any disclaimer, the term of this patent is extended or adjusted under 35 U.S.C. 154(b) by 0 days.

(21) Appl. No.: 18/460,637

(22) Filed: Sep. 4, 2023

(65) Prior Publication Data

US 2023/0405041 A1    Dec. 21, 2023

Related U.S. Application Data

(63) Continuation of application No. PCT/CN2022/078780, filed on Mar. 2, 2022.

(30) Foreign Application Priority Data

Mar. 4, 2021    (CN) .......................... 202110241981.9

(51) Int. Cl.
*A61K 31/728* (2006.01)
*A61P 25/00* (2006.01)
(Continued)

(52) U.S. Cl.
CPC ............ *A61K 31/728* (2013.01); *A61P 25/00* (2018.01); *A61P 25/28* (2018.01); *A61P 31/12* (2018.01)

(58) Field of Classification Search
CPC .... A61K 31/728; A61K 31/16; A61K 31/216; A61K 31/24; A61K 31/245; A61P 25/28; (Continued)

(56) References Cited

U.S. PATENT DOCUMENTS 4,419,365 A * 12/1983 McLachlan ............ A61K 31/16
514/575
5,217,998 A *  6/1993 Hedlund ................ A61K 31/16
514/777

(Continued)

FOREIGN PATENT DOCUMENTS

CN      1794999    6/2006
CN    101209259    7/2008
(Continued)

OTHER PUBLICATIONS

Li, J. et al."Ferroptosis: past, present and future" Cell Death Dis., vol. 11, No. 88, pp. 1-13. (Year: 2020).*
(Continued)

*Primary Examiner* — Eric Olson
(74) *Attorney, Agent, or Firm* — Piloff Passino & Cosenza LLP; Rachel Piloff; Sean Passino

(57) ABSTRACT

An application of hyaluronic acid in preparing medicines for preventing or treating ferroptosis-related diseases is provided, and an application of hyaluronic acid or salts of hyaluronic acid or derivatives of hyaluronic acid in prepar- (Continued)

ing medicines for inhibiting ferroptosis is also provided. According to the present application, the anti-ferroptosis function of hyaluronic acid is disclosed. The hyaluronic acid is the first natural extracellular matrix material with anti-ferroptosis function found at present. The hyaluronic acid is one of the components of natural extracellular matrix and exists in large quantities in human body and is also a widely used material in clinic.

5 Claims, 15 Drawing Sheets

(51) Int. Cl.
  *A61P 25/28* (2006.01)
  *A61P 31/12* (2006.01)
(58) Field of Classification Search
  CPC .......... A61P 13/12; A61P 25/00; A61P 25/14; A61P 25/16; A61P 39/04
  See application file for complete search history.

(56) References Cited

U.S. PATENT DOCUMENTS

| | | | |
|---|---|---|---|
| 5,674,857 A | 10/1997 | Falk | |
| 2006/0135439 A1 | 6/2006 | Kato | |
| 2010/0317616 A1* | 12/2010 | Prestwich | A61P 1/02 536/53 |
| 2018/0193353 A1* | 7/2018 | Gurtner | A61P 3/00 |
| 2019/0008984 A1* | 1/2019 | Buchman | A61P 19/08 |

FOREIGN PATENT DOCUMENTS

| | | | | |
|---|---|---|---|---|
| CN | 101626754 | | 1/2010 | |
| CN | 110464727 | | 11/2019 | |
| CN | 112972490 | | 6/2021 | |
| EP | 0208623 | | 1/1987 | |
| EP | 1611893 | | 4/2006 | |
| WO | 9529683 | | 11/1995 | |
| WO | 9725051 | | 7/1997 | |
| WO | 2004084912 | | 10/2004 | |
| WO | WO-2004084912 A1 * | 10/2004 | | A61K 31/70 |
| WO | 2006093957 | | 9/2006 | |

OTHER PUBLICATIONS

Mahaman, Y. et al."Biomarkers used in Alzheimer's disease . . . " Ageing Res. Rev., vol. 74, pp. 1-26. (Year: 2022).*
Ahya, K. et al."Neonatal periventricular leukomalacia . . . " Res. Rep. Neonatol., vol. 8, pp. 1-8. (Year: 2018).*
Wang, K. et al."HIF-1a and VEGF are involved in deferoxamine . . . " J. Surg. Res., vol. 246, pp. 419-426. (Year: 2020).*
Cepeda, S. et al "Traumatic intracerebral hemorrhage . . . " J. Neurotraum., vol. 32, pp. 1246-1253. (Year: 2015).*
Farr, A. et al."Challenges and opportunities of deferoxamine delivery . . . " Mol. Pharm., vol. 18, pp. 593-609. (Year: 2021).*
Ikeda, Y. et al."Iron chelation by deferoxamine prevents renal interstitial fibrosis . . . " Plos One, vol. 9, iss 2, pp. 1-10. (Year: 2014).*
Vignesh et al., "Injectable deferoxamine nanoparticles loaded chitosan-hyaluronic acid coacervate hydrogel for therapeutic angiogenesis" Colloids and Surfaces B: Biointerfaces vol. 161 pp. 129-138, DOI: 10.1016/j.colsurfb.2017.10.033 (Year: 2011).*
Mncenzo Liguori et al., "Double-blind, randomized clinical study comparing hyaluronic acid cream to placebo in patients treated with radiotherapy," Radiotherapy and Oncology 42 (1997) 155-161.
She Xu, "Ferroptosis and Nerve Injury in Stroke" Chinese Journal of Biochemistry and Molecular Biology, Jul. 2020, 36(7):756-765 (abstract).
Wang Ying et al., "Research Progress on Biomaterials for Treatment of Central Nervous System Injuries", Materials China, May 2012, vol. 31 No. 5, pp. 11-20 (abstract).
First Office action dated Sep. 15, 2021 from SIPO in CN 202110241981.9.
Second Office action dated Nov. 24, 2021 from SIPO in CN 202110241981.9.
Third Office action dated Dec. 14, 2021 from SIPO in CN 202110241981.9.
Fourth Office action dated Dec. 27, 2021 from SIPO in CN 202110241981.9.
(ISA/210) International Search Report dated Sep. 9, 2022 in PCT/CN2022/078780 with Translation of the ISR dated Sep. 9, 2022 in PCT/CN2022/078780.
(ISA/237) Written Opinion of the International Searching dated Sep. 9, 2022 in PCT/CN2022/078780.
Notification to Grant Patent Right for Invention dated Jan. 25, 2022 from SIPO in 202110241981.9.
Search report dated Dec. 29, 2021 from SIPO in 202110241981.9.
Retrieval Report from SIPO dated Aug. 11, 2021 in 202110241981.9.
Supplemental Retrieval Report from SIPO dated Sep. 27, 2021 in 202110241981.9.
Supplemental Retrieval Report from SIPO dated Dec. 20, 2021 in 202110241981.9.

* cited by examiner

APPLICATION OF HYALURONIC ACID IN PREPARING MEDICINES FOR PREVENTING OR TREATING FERROPTOSIS-RELATED DISEASES

CROSS-REFERENCE TO RELATED APPLICATIONS

This application is a continuation of PCT/CN2022/078780, filed on Mar. 2, 2022 and claims priority of Chinese Patent Application No. 202110241981.9, filed on Mar. 4, 2021, the entire contents of which are incorporated herein by reference.

TECHNICAL FIELD

The present application relates to the field of biomedicine, and in particular to an application of hyaluronic acid in preparing medicines for preventing or treating ferroptosis-related diseases.

BACKGROUND

Cell ferroptosis, a new programmed cell death form, was discovered in 2012, which is different from apoptosis, necrosis and autophagy in morphology, biochemistry and genetics. Because this process depends on the existence of iron ions, it is called ferroptosis. The mechanism of ferroptosis is the imbalance between the production and degradation of lipid reactive oxygen species in the inner membrane of cells, and the iron ions-dependent, oxidative and non-apoptotic programmed cell death. The typical characteristics are as follows: mitochondria become smaller, the density of bilayer membrane increases, and at the same time, the lipid reactive oxygen free radicals in cell membrane increase.

Since the ferroptosis was first reported, more and more studies have found that ferroptosis plays an important role in the pathological development of many diseases, including traumatic brain injury, cerebral hemorrhage, hemochromatosis, liver/kidney/heart diseases and so on. Therefore, anti-ferroptosis intervention has great potential value in treating many diseases. At present, the most commonly used ferroptosis inhibitors in research are deferoxamine (DFO) and ferrostatin-1(Fer-1). Among them, deferoxamine is an iron ion chelator, which is mainly used for treating acute iron poisoning in clinic. Fer-1 is still a compound only used for experimental research. At present, no natural biomaterials with anti-ferroptosis function have been found. The present application discovers the anti-ferroptosis function of hyaluronic acid material for the first time, and the hyaluronic acid material is capable of playing a synergistic role with known ferroptosis inhibitors such as DFO.

In view of this, the present application is proposed.

SUMMARY

The present application proposes an application of hyaluronic acid, hyaluronates or derivatives of hyaluronic acid in preparing medicines for preventing or treating ferroptosis-related diseases.

The present application also proposes an application of hyaluronic acid, hyaluronates or derivatives of hyaluronic acid in preparing medicines for inhibiting ferroptosis.

The present application also provides a ferroptosis inhibitor.

The present application also provides a ferroptosis inhibitor composition.

The present application also provides a ferroptosis inhibitor adjuvant.

The technical scheme of the present application has at least the following technical effects.

The present application discloses the anti-ferroptosis function of hyaluronic acid for the first time, which is the first natural extracellular matrix material with anti-ferroptosis function found at present. Hyaluronic acid is one of the components of natural extracellular matrix, which exists in large quantities in human body and is also a widely used material in clinic. Hyaluronic acid is easy to mass-produce, low in cost and good in safety. The new function of hyaluronic acid disclosed by the present application is of great value for the research and development of anti-ferroptosis related medical products.

In addition, hyaluronic acid, which has been approved by Food and Drug Administration (FDA)/China Food and Drug Administration (CFDA) to be applied in the clinic, is widely used in many fields such as drugs for arthritis treatment, eye drops, food additives, cosmetics, etc., and has good safety.

The application in the present application is capable of directly playing an anti-ferroptosis role, and is capable of being used as a medicine for treating diseases involving ferroptosis such as nerve injury. It can also be used in conjunction with existing ferroptosis inhibitors, such as DFO, for synergistic treatment of diseases involving ferroptosis. The present application provides an anti-ferroptosis treatment medicine and adjuvant with clinical prospect.

DETAILED DESCRIPTION OF THE EMBODIMENTS

Figure 1:
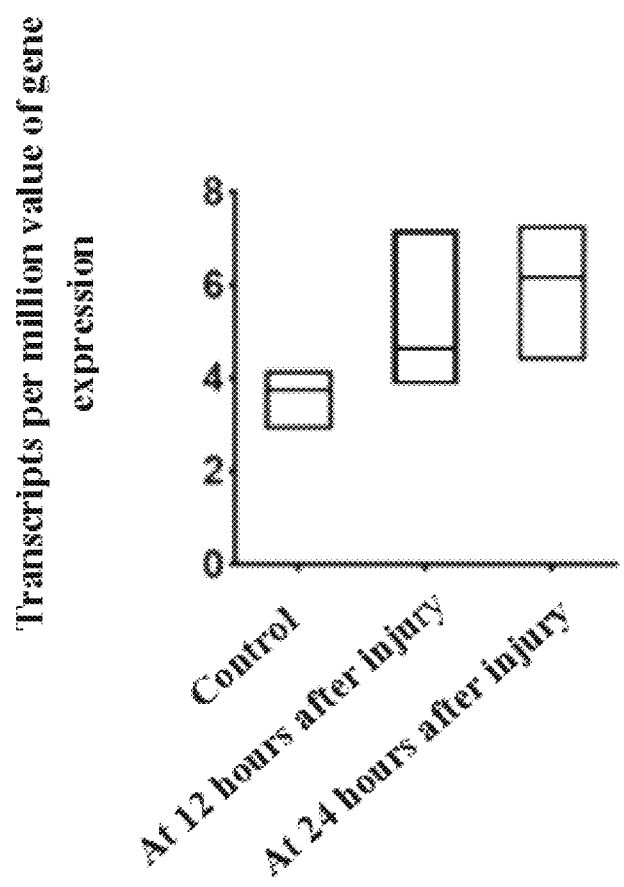
FIG. 1 shows an expression of ferroptosis regulatory gene Solute Carrier Family 7 Member 11 (SLC7A11) detected by RNA sequencing in brain injury tissues in an embodiment of the present application.

In order to explain the embodiments of the present application or the technical scheme in the prior art more clearly, in the following description, different "one embodiment" or "an embodiment" do not necessarily refer to the same embodiment. Different embodiments may be replaced or combined, and for those skilled in the art, other embodiments may be obtained according to these embodiments without creative labor.

After long-term and in-depth research, the inventor found the potential relationship between hyaluronic acid and ferroptosis in the deep RNA sequencing of traumatic brain tissue, and further proved the anti-ferroptosis function of hyaluronic acid through in vitro and in vivo experiments. At the same time, it is also found that hyaluronic acid may be used in combination with existing ferroptosis inhibitors such as DFO to treat diseases involving ferroptosis such as brain (nerve) injury.

Embodiments of the present application provide an anti-ferroptosis function of hyaluronic acid and a new application. Hyaluronic acid is one of the components of natural extracellular matrix, which has good safety. The embodiments of the present application relate to the application of hyaluronic acid, hyaluronates or derivatives of hyaluronic acid in preparing medicines for preventing or treating ferroptosis-related diseases. The embodiments also relate to the application of hyaluronic acid or salts of hyaluronic acid or derivatives of hyaluronic acid in preparing medicines for inhibiting ferroptosis. The new function of hyaluronic acid disclosed by the present application is of great value for the research and development of anti-ferroptosis related medical products.

The hyaluronic acid is natural or synthetic.

The hyaluronates are preferably soluble salts of hyaluronic acid, preferably a sodium salt of hyaluronic acid.

Preferably, the number-average molecular weight of hyaluronic acid or salts of hyaluronic acid ranges from 700 kilodaltons (kD) to 1500 kD.

Specifically, the derivatives of hyaluronic acid include a compound taking hyaluronic acid as the basic structural unit and modified by substituent, and the substituent may be selected from alkyl groups, alkoxy groups, hydroxyl groups, carboxyl groups, acyl groups, ester groups and the like.

Specifically, diseases caused by ferroptosis include brain injury, brain stroke, cerebral hemorrhage, ischemia-reperfusion injury, nerve injury, neurodegenerative diseases, hemochromatosis, liver diseases, renal failure, heart disease and iron metabolism-related diseases caused by abnormal levels of ferroptosis-related factors. Injuries include traumatic injuries and radiation injuries. One of the typical pathological features of the above diseases is cell ferroptosis, but there are no anti-ferroptosis products in clinical treatment at present. Therefore, hyaluronic acid, which has the function of inhibiting ferroptosis, may be a potential medicine for treating these diseases.

Neurodegenerative diseases include Alzheimer's disease, Parkinson's disease, Huntington's disease and motor nerve degeneration. Nerve injury includes brain periventricular leukomalacia. Ischemia-reperfusion injury includes myocardial ischemia-reperfusion injury, hepatic ischemia-reperfusion injury or renal ischemia-reperfusion injury. Iron metabolism-related diseases include atherosclerosis or diabetes.

Specifically, the dosage forms of medicines include tablets, powders, granules, capsules, injections, sprays, films, suppositories, nasal drops or dripping pills.

Specifically, the modes of medicine administration include intravenous injection, intraperitoneal injection, intramuscular injection, subcutaneous injection, oral administration, sublingual administration, nasal administration or transdermal administration.

The embodiments of the present application also relate to a ferroptosis inhibitor. The ferroptosis inhibitor contains at least one of a hyaluronates and derivatives of hyaluronic acid. Furthermore, the ferroptosis inhibitor also contains pharmaceutically acceptable excipients. The ferroptosis inhibitor of the present application may directly play an anti-ferroptosis role, and may be used as a medicine for treating diseases involving ferroptosis such as nerve injury.

The embodiments of the present application also relate to a ferroptosis inhibitor composition. The ferroptosis inhibitor composition contains hyaluronic acid or salts of hyaluronic acid or derivatives of hyaluronic acid and other ferroptosis inhibitors. Preferably, other ferroptosis inhibitors are selected from but not limited to deferoxamine and/or Ferrostatin-1. Furthermore, the ferroptosis inhibitor also contains pharmaceutically acceptable excipients. The ferroptosis inhibitor of the present application may also be used in cooperation with existing ferroptosis inhibitors, such as DFO, for synergistic treatment of diseases involving ferroptosis.

The embodiments of the present application also relate to a ferroptosis inhibitor adjuvant. The ferroptosis inhibitor adjuvant contains hyaluronic acid or salts of hyaluronic acid or derivatives of hyaluronic acid. Furthermore, the ferroptosis inhibitor also contains pharmaceutically acceptable excipients.

The embodiments of the present application also provide a method for inhibiting ferroptosis. The method for inhibiting ferroptosis specifically includes administering an effective amount of hyaluronic acid to an object in need of treatment. The embodiments of the present application also provide a method for preventing or treating ferroptosis-related diseases. The method for preventing or treating ferroptosis-related diseases specifically includes administering an effective amount of hyaluronic acid to an object in need of treatment. Specifically, methods for treating brain injury, brain stroke, cerebral hemorrhage, ischemia-reperfusion injury, nerve injury, neurodegenerative diseases, hemochromatosis, liver diseases, renal failure, heart disease and iron metabolism-related diseases caused by abnormal levels of ferroptosis-related factors are included. Injuries include traumatic injuries and radiation injuries. The neurodegenerative diseases include Alzheimer's disease, Parkinson's disease, Huntington's disease and motor nerve degeneration. The nerve injury includes brain periventricular leukomalacia. The ischemia-reperfusion injury includes myocardial ischemia-reperfusion injury, hepatic ischemia-reperfusion injury or renal ischemia-reperfusion injury. The Iron metabolism-related diseases include atherosclerosis or diabetes.

Before further describing the specific embodiments of the present application, it should be understood that the present application will be further described in detail through the following embodiments, so that those skilled in the art may further understand the present application, but the present application is not limited in any way.

Embodiment 1 Discovery and Proof of Anti-Ferroptosis Function of Hyaluronic Acid (1) C57 mouse (male, 20-25 g, Beijing Weitong Lihua Experimental Animal Center) is injected with 1% pentobarbital sodium solution (50 mg/Kg body weight) intraperitoneally, the hair above the skull is carefully removed with a bending scissors, a 1-2 cm incision is made along the midline skin of the head to expose the skull and remove the muscle tissue above the skull and a cranial drill is used to open a window with a diameter of about 2 mm in the left frontal parietal region (2 mm to the left and 3 mm to the front of the lambda) to expose the cerebral cortex. Subsequently, the impact injury is prepared at the above-mentioned exposure window by a precisely controlled cortical impactor (WILKERSON, USA), and the impact parameters are set as follows: at a speed of 3.5 m per second, impact depth of 1 mm and residence time of 0.5 second, and the scalp is sutured, and the mouse is stored and raised in a single cage after awakening.

(2) the brain tissue of the injured area is taken from above-mentioned brain injury model at 12 hours and 24 hours after injury, and the corresponding brain tissue of normal mouse is taken as a control.

(3) Brain tissues were pyrolyzed with TRIZOL (Life technologies), frozen at 80° C., and transported with dry ice to Guangzhou Magen Biotechnology Co., Ltd. for RNA sequencing.

(4) the sequencing data is analyzed, and the expression of different cell death markers, such as ferroptosis, necrosis and apoptosis, as well as the expression of different extracellular matrix components are analyzed, including expression of collagen, fibronectin, laminin and hyaluronic acid synthase 2 (HAS2).

Figure 2:
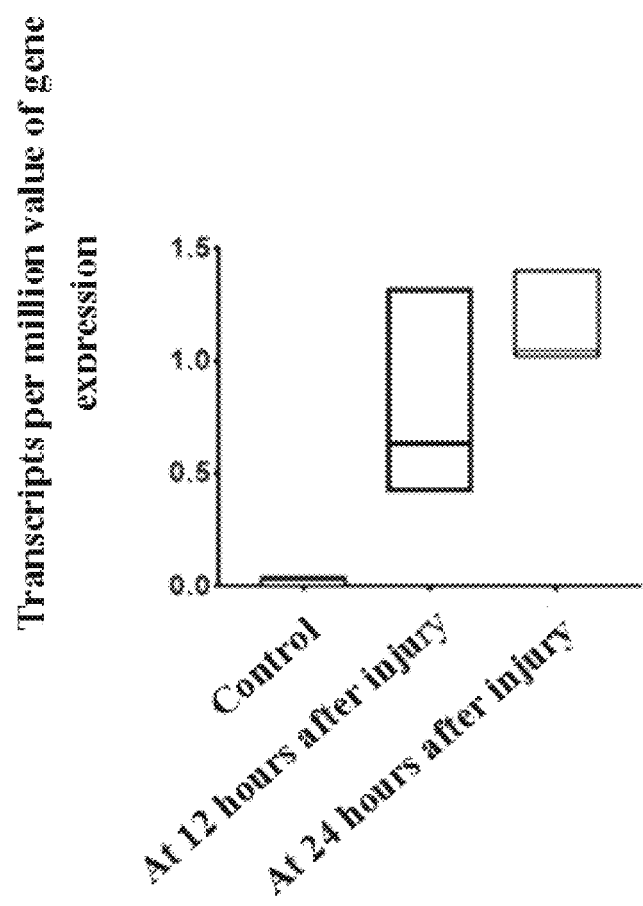
FIG. 2 shows an expression of hyaluronic acid synthase 2 (HAS2) detected by RNA sequencing in brain injury tissues in an embodiment of the present application.

The analysis results show that the expression patterns of HAS2 and ferroptosis marker SLC7A11 are highly similar after brain injury, as shown in FIG. 1 and FIG. 2.

Figure 3:
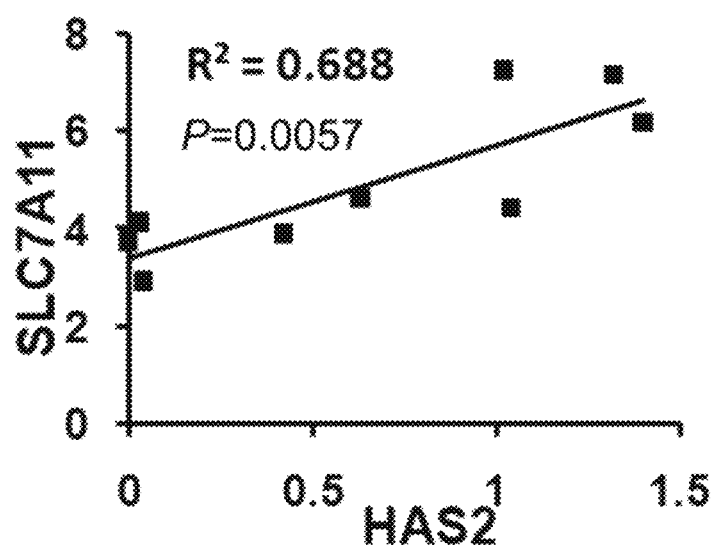
FIG. 3 is an analysis of a correlation between SLC7A11 expression and HAS2 expression in brain injury in an embodiment of the present application.

The expressions of HAS2 and SLC7A11 are analyzed by linear regression analysis, as shown in FIG. 3.

The results show that there is a significant correlation between HAS2 and SLC7A11 (P=0.0057), which indicates that hyaluronic acid is closely related to ferroptosis.

The neural cell lines HT22 (from American type culture collection) are taken as study objects.

Erastin (Merck Chemicals), $H_2O_2$ and staurosporine (Beijing Solarbio Science & Technology Co., Ltd.) are added to the culture medium, respectively, for induction to obtain a ferroptosis model (treated for 12 hours), a necrosis model (treated for 24 hours) and an apoptosis model (treated for 48 hours), respectively. At the same time, sodium hyaluronate (number-average molecular weight: 1500 kD, Bloomage BioTech Co., Ltd.) with a final concentration of 0.1% is added to different cell death model culture solution. Cell viability is detected by CCK8 kit (Bimake Biotechnology Co., Ltd., USA), and the protective effect of sodium hyaluronate on HT22 cells under the conditions of ferroptosis, necrosis and apoptosis is analyzed.

Figure 4:
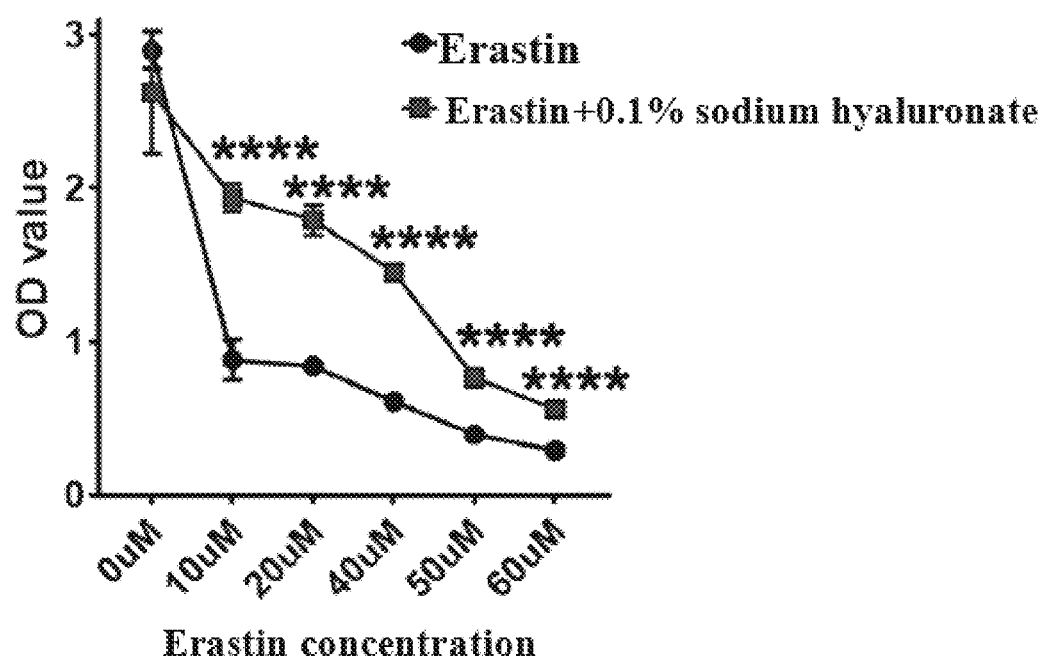
FIG. 4 shows an effect of sodium hyaluronate on ferroptosis of hippocampal neuronal cells (HT22) in an embodiment of the present application (****$P<0.0001$).
Figure 5:
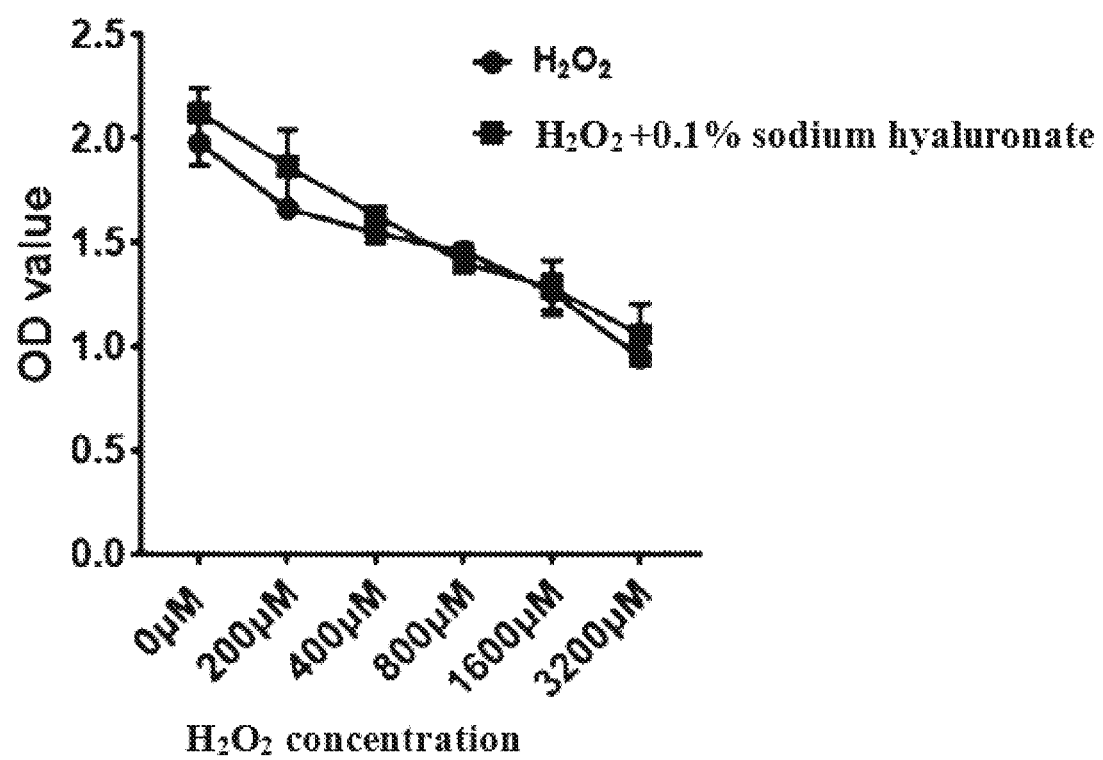
FIG. 5 shows an effect of sodium hyaluronate on $H_2O_2$ (hydrogen peroxide)-induced HT22 cell necrosis model in an embodiment of the present application (****$P<0.0001$).
Figure 6:
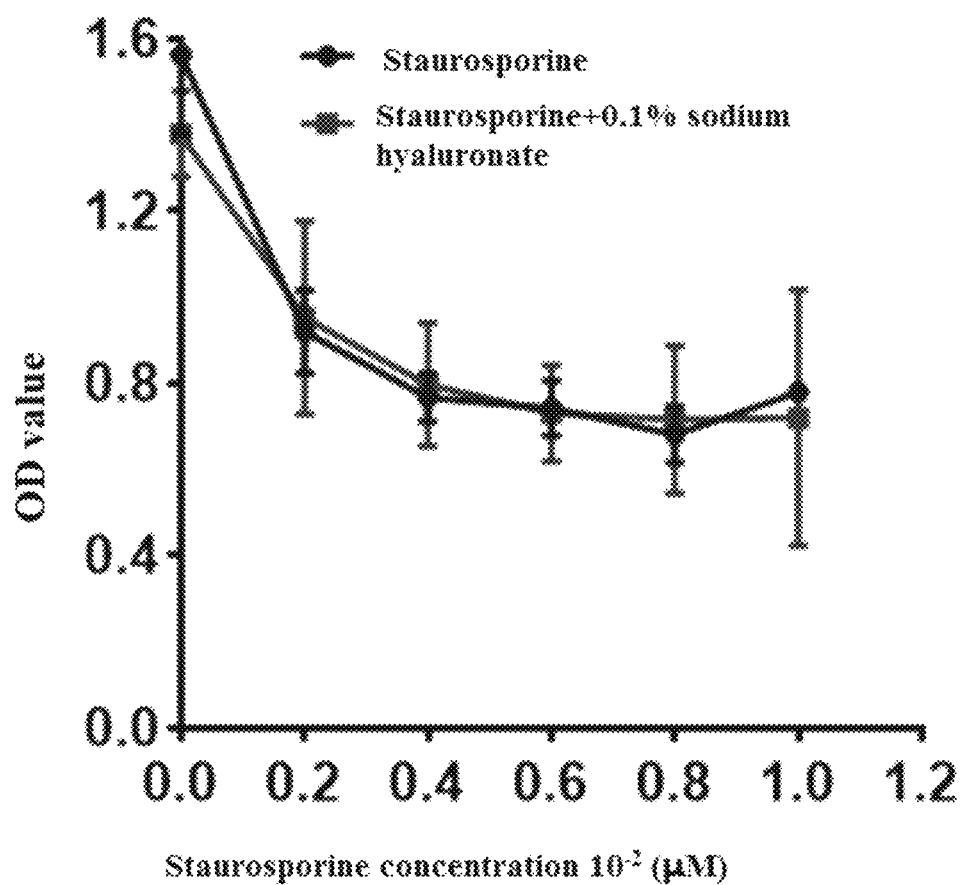
FIG. 6 shows an effect of sodium hyaluronate on staurosporine-induced HT22 cell apoptosis model (****$P<0.0001$).

From the results as shown in FIG. 4-FIG. 6, the addition of sodium hyaluronate significantly inhibits the occurrence of HT22 ferroptosis induced by different concentrations of Erastin. However, the addition of sodium hyaluronate has no effect on the necrosis (as shown in FIG. 5) and apoptosis (as shown in FIG. 6) of HT22 cells. The results show that hyaluronic acid has the function of anti-ferroptosis.

Embodiment 2: Optimal Molecular Weight and Concentration of Hyaluronic Acid Anti-Ferroptosis (1) Sodium hyaluronate with number-average molecular weights of 40 kD, 170 kD, 470 kD, 730 kD, 1500 kD and 2300 kD come from Bloomage BioTech Co., Ltd., and sodium hyaluronate with number-average molecular weights of 1000 kD came from Beijing Solarbio Science & Technology Co., Ltd.

Figure 7:
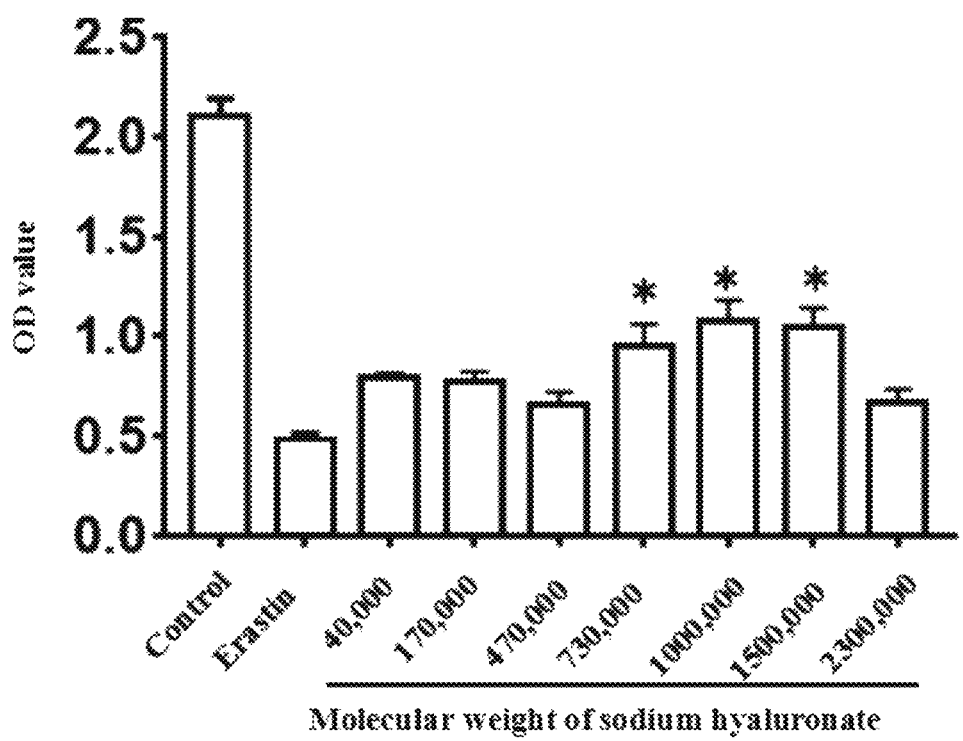
FIG. 7 shows an influence of a molecular weight of sodium hyaluronate on anti-ferroptosis function of sodium hyaluronate (* indicates that compared with other molecular weights, $P<0.05$).

(2) HT22 cells are inoculated into a 48-well plate at a rate of $2\times10^4$/well. The next day, the culture solution is changed and 50 μM Erastin is added to induce ferroptosis. Different groups are set, and 0.1% sodium hyaluronate with different molecular weights is added to the culture solution containing Erastin. After treatment for 12 hours, CCK8 solution is added for incubation for 2 hours, and the optical density (OD) value is determined by a Microplate Reader. As shown in FIG. 7, sodium hyaluronate with different molecular weights has protective effects on the viability of HT22 cells. The results show that sodium hyaluronate with molecular weight of 730 KD-1500 KD has a good protective effect on cell viability. Accordingly, the optimal molecular weight of sodium hyaluronate anti-ferroptosis is 700 kD-1500 kD.

Figure 8:
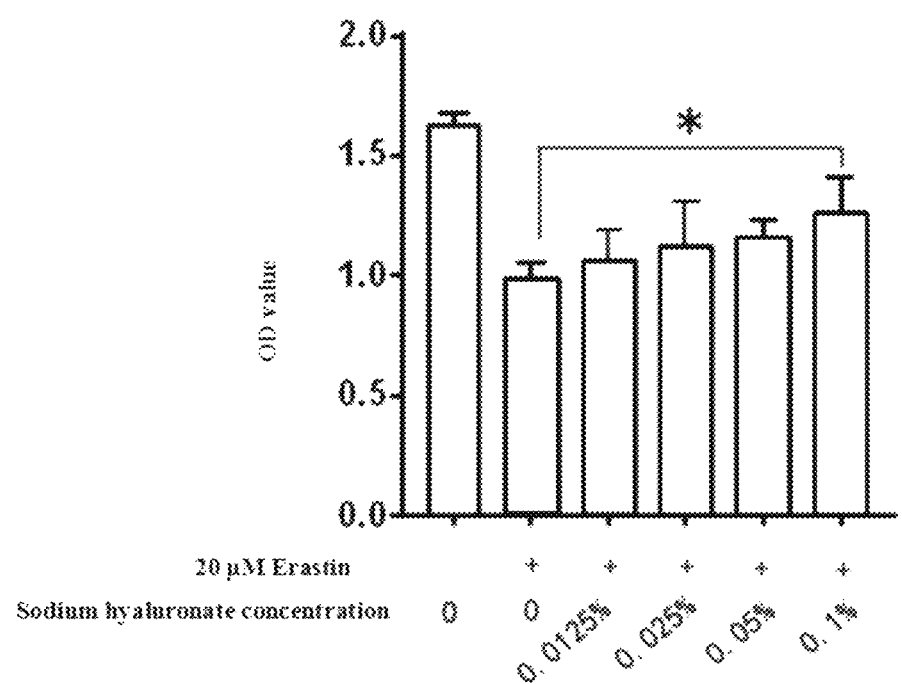
FIG. 8 shows an influence of sodium hyaluronate concentration of 0.0125% to 0.1% on anti-ferroptosis function of sodium hyaluronate ($P<0.05$) in an embodiment of the present application.
Figure 9:
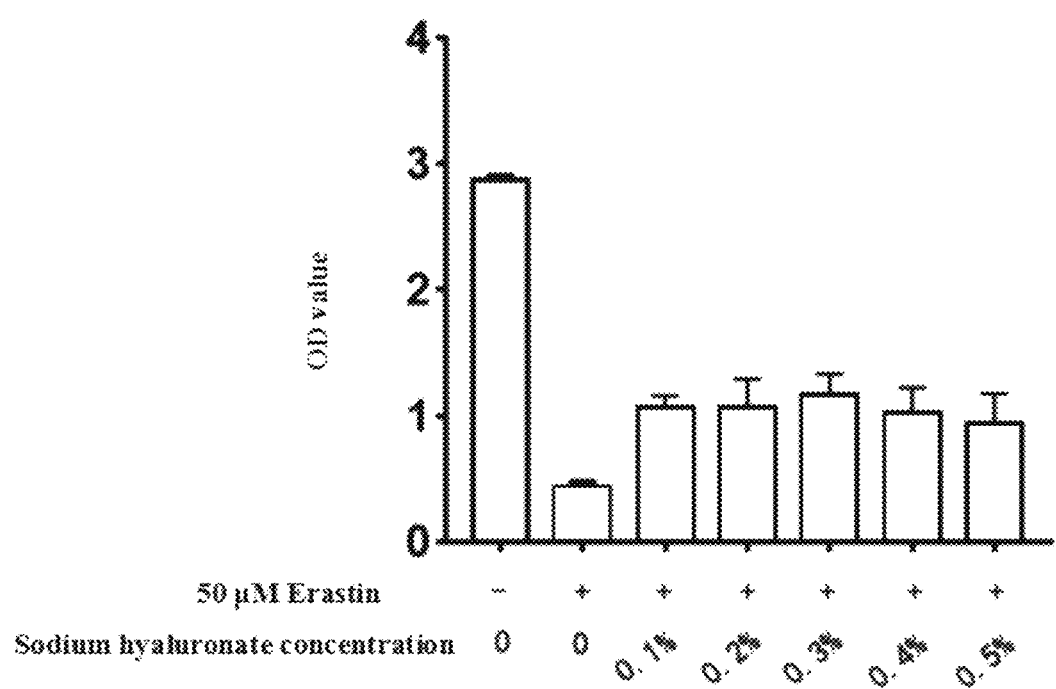
FIG. 9 shows an influence of sodium hyaluronate concentration of 0.1% to 0.5% on anti-ferroptosis function of sodium hyaluronate ($P<0.05$) in an embodiment of the present application.

(3) HT22 cells are inoculated into a 48-well plate at a rate of $2\times10^4$/well. The next day, the culture solution is changed and 20 μM Erastin is added to induce ferroptosis. Different groups are set, 0.01%, 0.025%, 0.05% and 0.1% sodium hyaluronate (1500 kD) are added to the culture solution containing Erastin. After treatment for 12 hours, then CCK8 solution is added for incubation for 1.5 hours, and the OD value is determined by the Microplate Reader. As shown in FIG. 8, with the increase of sodium hyaluronate concentration, the cell viability increases, and 0.1% sodium hyaluronate has the best anti-ferroptosis effect. In order to further determine the anti-ferroptosis effect of hyaluronic acid, HT22 cells are inoculated into a 48-well plate at a rate of $2\times10^4$/well, and the culture solution is changed the next day, and 50 μM Erastin is added to induce ferroptosis. Sodium hyaluronate with concentrations of 0.1%, 0.2%, 0.3%, 0.4% and 0.5% is added to the culture solution containing Erastin respectively. As shown in FIG. 9, there is no significant difference in cell viability between the 0.1% concentration sodium hyaluronate treatment group and the higher concentration sodium hyaluronate treatment group, indicating that the 0.1% concentration reaches the best anti-ferroptosis function of sodium hyaluronate, and the further increase of the concentration cannot further enhance its anti-ferroptosis function. The results show that the optimal concentration of sodium hyaluronate for anti-ferroptosis is 0.1%.

Embodiment 3: Synergistic Effect of Anti-Ferroptosis Function of Hyaluronic Acid and Deferoxamine (DFO, Merck Chemicals)

Figure 10:
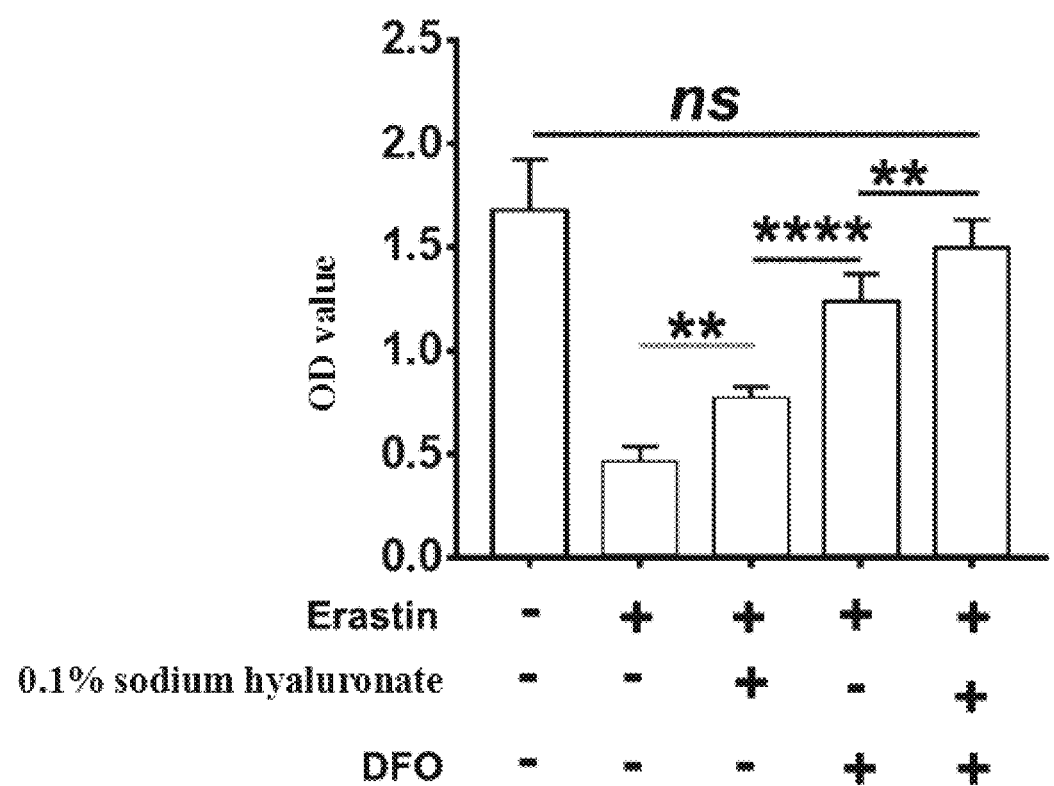
FIG. 10 shows a synergistic effect of sodium hyaluronate and deferoxamine (DFO) in anti-ferroptosis in an embodiment of the present application.

HT22 cells are inoculated in a 48-well plate at a rate of $2\times10^4$/well. The next day, different groups are set: normal culture group, 50 μM Erastin treatment group, 50 μM Erastin+0.1% sodium hyaluronate treatment group, 50 μM Erastin+20 μM DFO treatment group, and 50 μM Erastin+0.1% sodium hyaluronate+20 μM DFO treatment group. After 12 hours of treatment, CCK8 solution is added to incubate for 2 hours, and the OD value is determined by microplate reader. As shown in FIG. 10, both sodium hyaluronate alone and DFO alone have anti-ferroptosis function, and they have obvious synergistic effect when combined together. Among the ferroptosis cell models induced by 50 μM Erastin, 0.1% sodium hyaluronate+20 μM DFO significantly saves the ferroptosis of cells, and keeps the cell viability at a similar level to cell viability of normal cultured cells, which is significantly superior to the protective effects of sodium hyaluronate alone and DFO alone.

Embodiment 4: Application of Anti-Ferroptosis Function of Hyaluronic Acid in Brain Injury C57 mouse (male, 20-25 g, Beijing Weitong Lihua Experimental Animal Center) is injected with 1% pentobarbital sodium solution (50 mg/Kg body weight) intraperitoneally, the hair above the skull is carefully removed with a curved scissors, a 1-2 cm incision is made along the midline skin of the head to expose the skull, remove the muscle tissue above the skull, and a cranial drill is used to open a window with a diameter of about 2 mm in the left frontal parietal region (2 mm to the left and 3 mm to the front of the lambda) to expose the cerebral cortex. Subsequently, the impact injury is prepared at the above-mentioned exposure window by a precisely controlled cortical impactor, and the impact parameters are set as follows: at a speed of 3.5 m per second, impact depth of 1 mm and residence time of 0.5 second.

Animal models are randomly divided into three groups: no treatment group, sodium hyaluronate dressing treatment group and sodium hyaluronate/DFO combined treatment group. Among them, in the no treatment group, the scalp is sutured directly without any treatment after trauma. In the sodium hyaluronate dressing treatment group, 50 μL of 3% sodium hyaluronate gel (prepared with normal saline, number-average molecular weight 1500 KD) is applied to the trauma surface, and then the scalp is sutured. In the sodium hyaluronate/DFO combined treatment group, 1 mM DFO medicine is dissolved in 3% hyaluronic acid gel at the same time, and 50 μL is applied to the trauma surface, and then the scalp is sutured.

Figure 11:
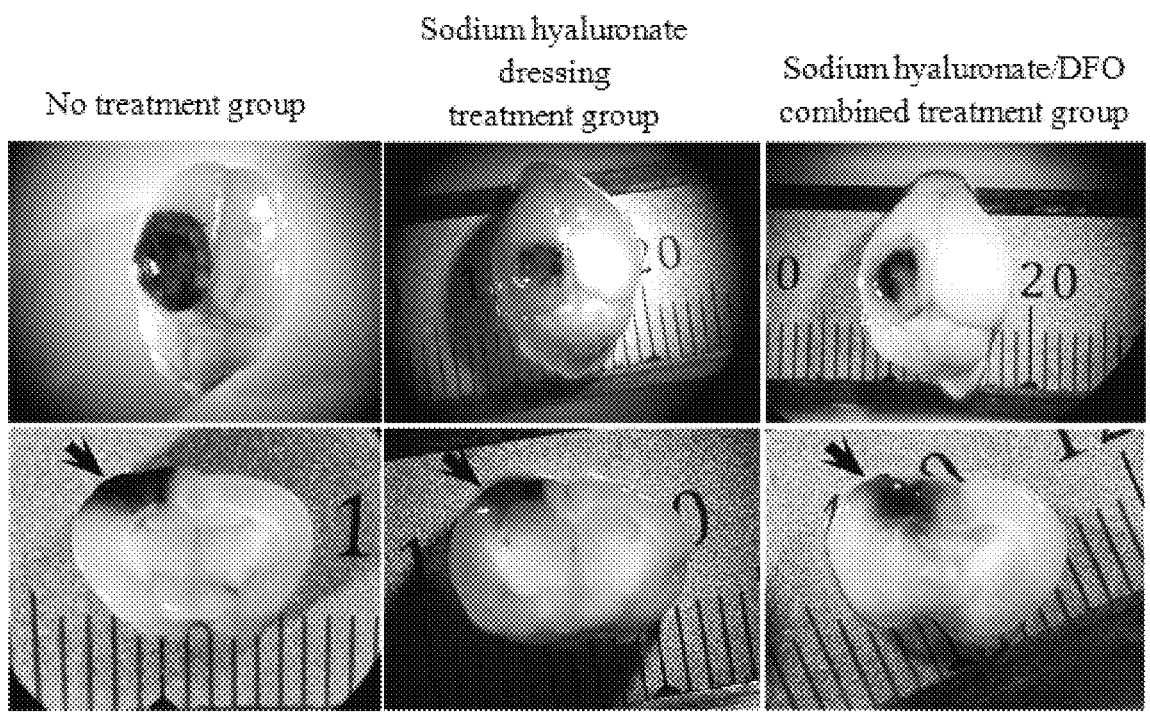
FIG. 11 shows protective effects of sodium hyaluronate dressing and sodium hyaluronate/DFO dressing on an integrity of blood-brain barrier after brain injury in an embodiment of the present application.

After 12 hours of treatment, 100 μL of 2% Evans blue staining solution is injected into the tail vein, and after 2 hours, the material of brain is taken to observe the blood-brain barrier destruction in different treatment groups. As shown in FIG. 11, the blood-brain barrier of animals in no treatment group is significantly destroyed, and a large number of Evans blue staining areas are observed in and around the trauma area, which were deeply stained. In the sodium hyaluronate dressing treatment group, the Evans blue staining area is significantly reduced and the staining degree is significantly reduced, indicating that sodium hyaluronate treatment has obvious protective effect on the blood-brain barrier of brain trauma. The results of sodium hyaluronate/DFO treatment group are similar to those of sodium hyaluronate alone treatment group, which indicates the protective effect on blood-brain barrier.

Figure 12:
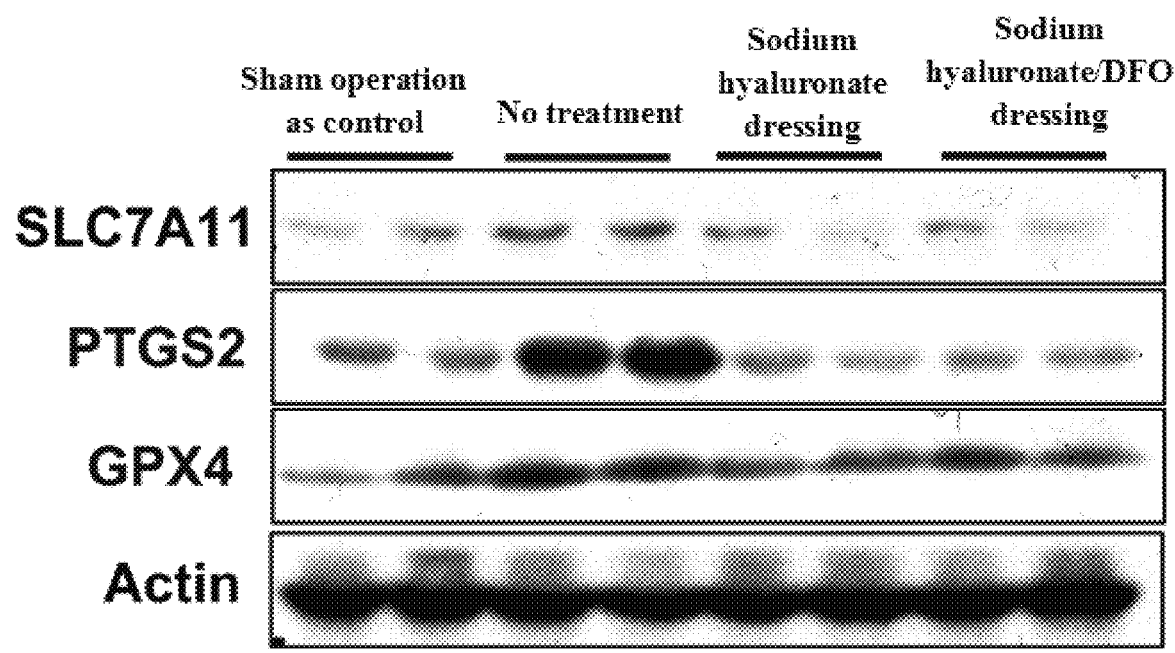
FIG. 12 shows an inhibitory effect of sodium hyaluronate dressing and sodium hyaluronate/DFO dressing on ferroptosis-related markers after brain injury in an embodiment of the present application.

24 hours after treatment, the brain tissues of injured areas in different treatment groups are taken, and the intact sham operation group is used as the control. Tissue protein is extracted by routine methods, and the expression level of ferroptosis-related markers is detected by Westrn Blotting. As shown in FIG. 12, compared with the control group, SLC7A11, prostaglandin endoperoxide synthase 2 (PTGS2), glutathione peroxidase 4 (GPX4) (antibodies are all from Abcam) related to ferroptosis after brain injury are significantly increased in the no treatment group, while are significantly inhibited in sodium hyaluronate dressing treatment group and sodium hyaluronate/DFO combined dressing treatment group, which indicates that the above dressing significantly inhibit the ferroptosis of nerve cells after brain injury.

Figure 13:
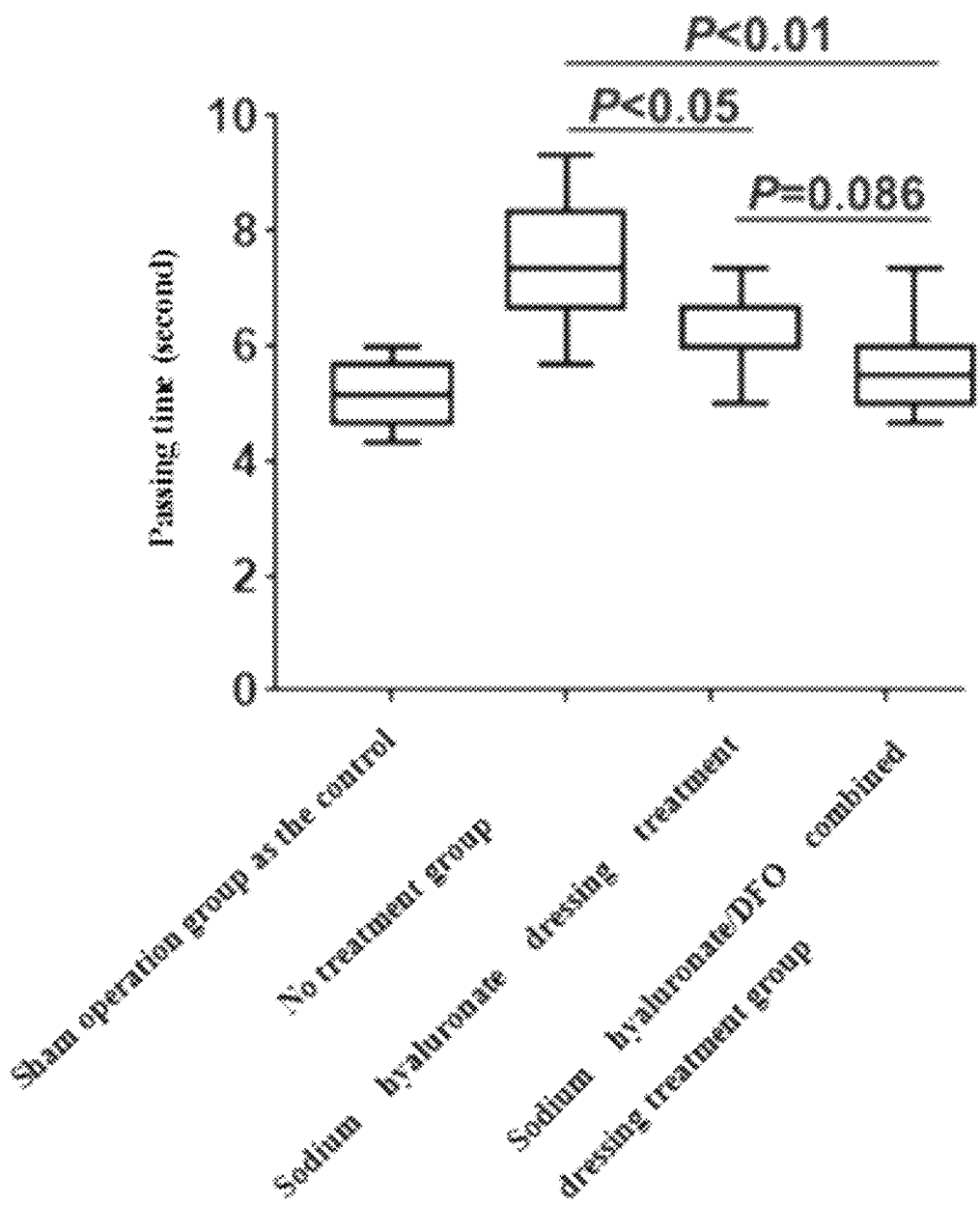
FIG. 13 shows effects of sodium hyaluronate dressing and sodium hyaluronate/DFO dressing treatment on animal behavioral ability after brain injury in an embodiment of the present application.

Three weeks after treatment, the animal's behavioral ability is evaluated by balance beam test. As shown in FIG. 13, the balance beam test show that the sodium hyaluronate dressing alone treatment ($P<0.05$) and sodium hyaluronate/DFO combined dressing treatment ($P<0.01$) significantly improve the animal's motor ability, indicating that the brain function is obviously protected. Although the balance beam test does not show significant difference ($P=0.086$) between the sodium hyaluronate dressing alone and sodium hyaluronate/DFO combined dressing by statistical analysis, from the results and the P value (close to 0.05), it can be seen that the sodium hyaluronate/DFO combined dressing improves the animal's behavioral ability better, indicating that sodium hyaluronate and DFO play a synergistic role.

Embodiment 5: Anti-Ferroptosis Effect of Hyaluronic Acid on Other Tissues and Cells Human embryonic kidney cells (293T) (from ATCC) and human lung epithelial cells (BEAS-2B) (from ATCC) are studied respectively. The above cells are inoculated into a 48-well culture plate in the amount of $2\times10^4$/well, and cultured in dulbecco's modified eagle medium (DMEM)+10% fetal bovine serum culture solution normally.

Figure 14:
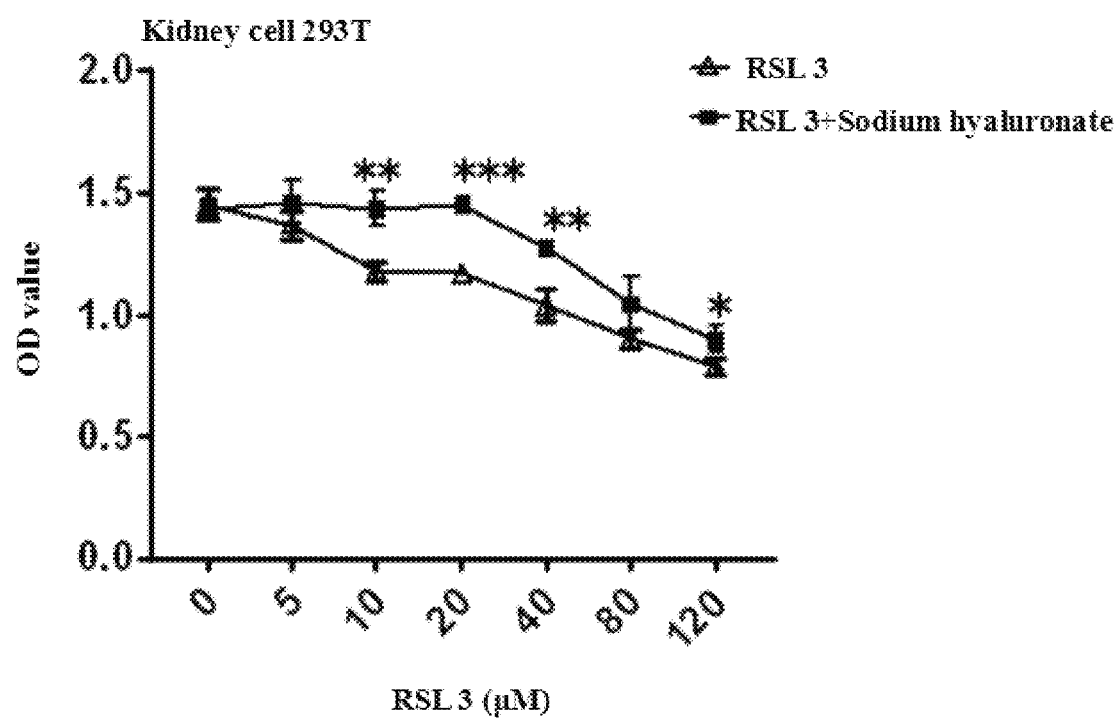
FIG. 14 shows an anti-ferroptosis effect of sodium hyaluronate on kidney cell 293T in an embodiment of the present application ($*p<0.05$; $P<0.01$; $*P<0.001$).
Figure 15:
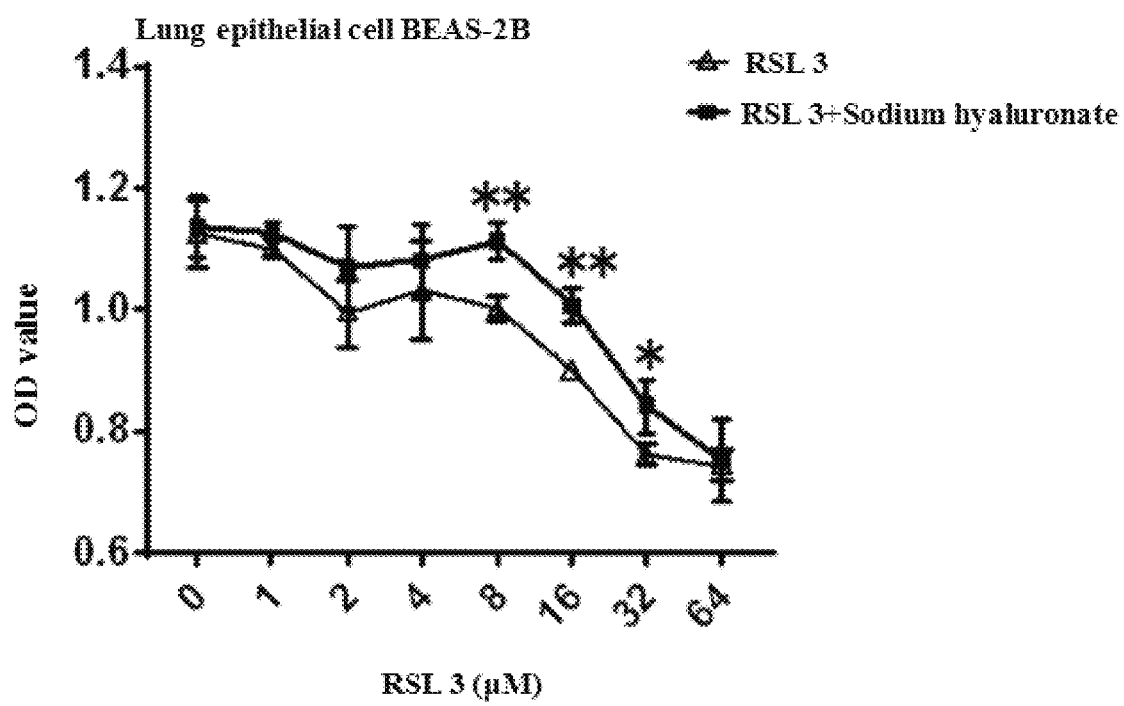
FIG. 15 shows an anti-ferroptosis effect of sodium hyaluronate on human normal lung epithelial cell BEAS-2B in an embodiment of the present application ($*P<0.05$; $**P<0.01$).

After 12 hours, the cells are completely adhered to the wall, and some cell samples are induced by ferroptosis inducer RSL3 (Merck Chemicals) with different concentrations. Other cell samples are given the same concentration of RSL3 to induce ferroptosis, while adding sodium hyaluronate (molecular weight 1500 kD) with a concentration of 0.1% for protection. After above cell samples are treated for 12 hours in a 5% carbon dioxide incubator at 37° C., CCK8 solution is added according to the instructions of the kit for incubation for 2 hours, and the OD value is determined and the cell viability is compared. As shown in FIG. 14, for 293T kidney cells, under the same concentration of RSL3, the addition of sodium hyaluronate significantly slows down the decline of cell viability, indicating that sodium hyaluronate reduces the ferroptosis of 293T. As shown in FIG. 15, for the lung epithelial cell BEAS-2B, under the same concentration of RSL3 ((1S,3R)-methyl 2-(2-chloroacetyl)-1-(4-(methoxycarbonyl)phenyl)-2,3,4,9-tetrahydro-1H-pyrido[3,4-b]indole-3-carboxylate), the addition of sodium hyaluronate significantly slows down the decline of cell viability, indicating that sodium hyaluronate reduces the ferroptosis of BEAS-2B. The above results indicate that hyaluronic acid has anti-ferroptosis effect on different types of tissues and cells.

Although the present application has been disclosed in terms of preferred embodiments, it is not intended to limit the claims. Any person skilled in the art may make some possible changes and modifications without departing from the concept of this application, so the scope of protection of this application should be based on the scope defined in the claims of this application.

What is claimed is:

1. A method for inhibiting ferroptosis, including administering an effective amount of an anti-ferroptosis medicine comprising hyaluronic acid or hyaluronates to an object in need of treatment, wherein a number-average molecular weight of the hyaluronic acid or the hyaluronates ranges from 730 kD-1500 kD and concentration of hyaluronic acid or its salts ranges from 0.1% to 0.5% weight/volume, wherein the medicines are used for treating cerebral hemorrhage or treating renal failure or treating a neurodegenerative disease; wherein the medicine further comprises ferroptosis inhibitors selected from the group consisting of deferoxamine or Ferrostatin-1 and pharmaceutically acceptable excipients.

2. The method according to claim 1, wherein the hyaluronic acid is natural or synthetic.

3. The method according to claim 1, wherein the hyaluronates are soluble salts of the hyaluronic acid.

4. The method according to claim 3, wherein the hyaluronates are sodium hyaluronate, potassium hyaluronate and zinc hyaluronate.

5. The method according to claim 1, wherein dosage forms of the medicines comprise tablets, powders, granules, capsules, injections, sprays, films, suppositories, nasal drops or dripping pills; or modes of medicine administration comprise intravenous injection, intraperitoneal injection, intramuscular injection, subcutaneous injection, oral administration, sublingual administration, nasal administration or transdermal administration.

* * * * *